(12) United States Patent
Hillebrand

(10) Patent No.: US 10,519,435 B2
(45) Date of Patent: Dec. 31, 2019

(54) METHOD FOR THE SELECTIVE SIZE-FRACTIONATED SEPARATION AND ISOLATION OF NUCLEIC ACID MIXTURES

(71) Applicant: aj Innuscreen GmbH, Berlin (DE)

(72) Inventor: Timo Hillebrand, Hoppegarten (DE)

(73) Assignee: AJ INNUSCREEN GmbH, Berlin (DE)

( * ) Notice: Subject to any disclaimer, the term of this patent is extended or adjusted under 35 U.S.C. 154(b) by 32 days.

(21) Appl. No.: 15/524,966

(22) PCT Filed: Nov. 9, 2015

(86) PCT No.: PCT/EP2015/076075
§ 371 (c)(1),
(2) Date: Nov. 17, 2017

(87) PCT Pub. No.: WO2016/071535
PCT Pub. Date: May 12, 2016

(65) Prior Publication Data
US 2018/0208923 A1     Jul. 26, 2018

(30) Foreign Application Priority Data
Nov. 7, 2014   (DE) .................. 10 2014 222 810

(51) Int. Cl.
*C12N 15/10* (2006.01)
*C07H 1/08* (2006.01)
*C12Q 1/68* (2018.01)

(52) U.S. Cl.
CPC ........... *C12N 15/1017* (2013.01); *C07H 1/08* (2013.01); *C12Q 1/68* (2013.01); *C12Q 2527/119* (2013.01); *C12Q 2563/137* (2013.01)

(58) Field of Classification Search
CPC . C12Q 1/68; C12Q 2527/119; C12Q 563/137
See application file for complete search history.

(56) References Cited

U.S. PATENT DOCUMENTS

| 2003/0198964 A1* | 10/2003 | Liu .......................... C12Q 1/68 435/6.11 |
| 2011/0130558 A1 | 6/2011 | Ritt et al. |
| 2011/0160446 A1 | 6/2011 | Ritt et al. |
| 2014/0243216 A1 | 8/2014 | Fabis et al. |
| 2015/0166592 A1 | 6/2015 | Guo |
| 2016/0024490 A1 | 1/2016 | Sperling et al. |

FOREIGN PATENT DOCUMENTS

| EP | 2 128 169 A1 | 12/2009 |
| WO | 2013/045434 A1 | 4/2013 |
| WO | 2013/181651 A1 | 12/2013 |
| WO | 2014/122288 A1 | 8/2014 |

OTHER PUBLICATIONS

International Search Report dated Apr. 28, 2016 in PCT/EP2015/076075 filed Nov. 9, 2015.

* cited by examiner

*Primary Examiner* — Pancham Bakshi
(74) *Attorney, Agent, or Firm* — Grünberg and Myers PLLC

(57) ABSTRACT

The invention relates to a method for size-fractionated isolation of nucleic acids, characterized by the following steps: —a first binding buffer, which contains at least one chaotropic salt and at least one substance that raises the pH of the binding buffer, is added—in the absence of aliphatic alcohols—to a volume of the mixture of nucleic acids, —binding on a solid phase and separation of the nucleic acids bound by step a), —a second binding buffer, which has a lower pH than the binding buffer under Point a), or a nonionic surfactant or an alcohol or a mixture of nonionic surfactant and alcohol is mixed with the filtrate from step a), —binding on a solid phase and separation of the nucleic acids bound by step c), —washing and elution, according to known methods, of the nucleic acid isolated after steps a) and c), with the result that the nucleic acids isolated after step a) not only have a larger number of base pairs than the nucleic acids isolated under step c), but also that, both after both step a) and after step c), individual, particular nucleic acid fractions with a particular number of base pairs are isolated that were not isolated in the respective other step. The size ratios of the nucleic acid fractions can be controlled by changing the pH.

8 Claims, 12 Drawing Sheets
Specification includes a Sequence Listing.

Fig. 4

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: PCR Primer CyB S

<400> SEQUENCE: 1
ccagcyccat caaacatctc akcatgatg                          29

<210> SEQ ID NO 2
<211> LENGTH: 36
<212> TYPE: DNA
<213> ORGANISM: Artificial Sequence
<220> FEATURE:
<223> OTHER INFORMATION: PCR Primer CyB AS

<400> SEQUENCE: 2
ttggctgagt ggtcggaata ttatgctkcg ttgytt                  36

METHOD FOR THE SELECTIVE SIZE-FRACTIONATED SEPARATION AND ISOLATION OF NUCLEIC ACID MIXTURES

The invention relates to a novel method for size-fractionated separation and isolation of nucleic acid mixtures.

The objective of the invention is in particular applications in which it is desired that only nucleic acids of a selected size spectrum be isolated, so that specific downstream applications may be carried out more efficiently. However, the invention is also suitable for the case in which users wish to analyze different nucleic acid fractions from a sample.

At present, a large number of commercially available kits exist for purification and recovery of nucleic acids, especially of DNA or of DNA fragments All of these methods are based on a method for preparative and analytical purification of DNA fragments from agarose gels, developed and described for the first time by Vogelstein and Gillespie (Proc. Natl. Acad. Sci. USA, 1979, 76, 615-619). The method combines the dissolution of the agarose containing the DNA bands to be isolated in a saturated solution of a chaotropic salt (NaI), with binding of the DNA on glass particles. The DNA fixed on the glass particles is then washed with a washing solution (20 mM Tris HCl [pH 7.2]; 200 mM NaCl; 2 mM EDTA; 50% v/v ethanol) and finally is detached from the carrier particles.

The physicochemical principle of this form of specific binding of nucleic acids on mineral carrier materials is believed to lie in the disruption of higher-level structures of the aqueous medium, with the result that the nucleic acids are adsorbed on the surface of mineral materials, especially of glass or silica particles. This disruption of the higher-level structures of the aqueous medium always takes place in the presence of chaotropic ions and is almost quantitative at high concentrations thereof. Since 1998, it has additionally been known that binding of nucleic acids on mineral carriers is entirely possible even without buffers containing chaotropic salts. For example, it is disclosed in patent disclosure WO2007/036564 A2 that even buffers containing so-called anti-chaotropic salts permit specific adsorption of nucleic acids on mineral carriers, whereby the process of isolation of nucleic acids is implemented by analogy with the known method based on chaotropic chemistry. Even this binding chemistry was subsequently optimized and refined (WO2007/060248 A1).

Published specification WO 01/62976 A1 discloses a method that describes the purification of nucleic acids from different reaction mixtures by addition of different alcohols, their subsequent precipitation on special solid phases (membranes with specific physical characteristics), washing steps with alcoholic buffers and final elution of the nucleic acids by means of water.

Likewise, patent specifications U.S. Pat. No. 5,405,951 A and EP 0512767 B1 describe the isolation of nucleic acids by incubation of the sample containing nucleic acid with an alcohol and subsequent incubation of the sample with a mineral material. The nucleic acids are eluted by addition of water heated to 60° C.

Patent specification DE 10253351 B4 discloses that the purification and recovery of nucleic acids is achieved by adjusting the solution containing nucleic acid with additives, to the effect that it contains monovalent and multivalent cations as well as an alcohol, then bringing it into contact with the solid phase, washing the carrier if necessary and detaching the nucleic acid from the solid phase. Ammonium chloride, sodium chloride and/or potassium chloride are used as the monovalent salt components and magnesium chloride, calcium chloride, zinc chloride and/or manganese chloride are used as the multivalent salt components.

It is disclosed that precisely the combination of a monovalent and a multivalent salt causes nucleic acids to be adsorbed on solid phases, while the ionic strength necessary for the purpose only has to be very low. This has the advantage that washing steps that may always have been necessary heretofore are no longer needed and thus the method for isolation of nucleic acids can be greatly shortened and simplified.

Patent disclosure WO2007/065934 A1 discloses a method that likewise permits purification of long-chain and short-chain DNA fragments, wherein the use of salts of citric acid yields buffers that have only low ionic strengths, so that washing steps are likewise no longer necessary.

All of these various methods exhibit a common feature. They always permit the isolation of a total nucleic acid contained in a sample. This means that, if a mixture of long-chain and short-chain nucleic acids is present in a sample, it is always purified as a mixture of nucleic acids. No separation or differential extraction of long-chain and short-chain nucleic acid fragments takes place, nor does selective purification of nucleic acids within a desired size spectrum.

Modern diagnostic issues now define the need to enrich or deplete particular nucleic acid fractions selectively in a sample containing nucleic acids or to obtain these fractions in differentiated form. Within the meaning of the present invention, a nucleic acid fraction is to be understood as a size fraction of the nucleic acid, i.e. short chain, longer-chain or long-chain nucleic acids.

Enrichment of short-chain nucleic acids and associated therewith depletion of longer-chain and long-chain nucleic acids from a sample plays a major role in modern prenatal diagnostics. What is desired is size-fractionated separation of freely circulating maternal DNA from freely circulating fetal DNA in the blood of pregnant women. The use of freely circulating fetal DNA for a prenatal diagnosis (e.g. detection of trisomy) has the advantage that an invasive examination (amniocentesis or chorionic villus biopsy), which always represents a risk for the growing fetus, would not be necessary. It is also known to the person skilled in the art, however, that the proportion of freely circulating DNA of fetal origin in the mother's blood is generally very much smaller than the proportion of freely circulating DNA of the mother. The large preponderance of maternal DNA greatly hampers the investigation of target sequences of the fetus, especially during DNA sequencing.

Furthermore, the proportion of freely circulating DNA is generally always very low, which additionally hampers a diagnosis, since a sufficient quantity of DNA cannot always be obtained. Here it would be desirable to be able to use greater sample volumes for extraction. Besides prenatal diagnostics, the isolation of freely circulating nucleic acid from body fluids is playing an increasingly larger role. This concerns molecular tumor diagnostics, the investigation of transplant rejection reactions and many more issues. In these research fields also, increasingly more interest is being shown in the ability to perform selective size-fractionated extraction of nucleic acids from a sample. In turn, it is also important that sufficient quantities of nucleic acids can be isolated and that for this reason larger sample volumes can be processed simply and rapidly. It is also important to investigate in general how the size distribution of nucleic acids in a sample appears, since conclusions on the origin of freely circulating DNA can be drawn from this.

WO2009/146776 A2 discloses a method that describes the isolation/purification of short-chain nucleic acids from a starting mixture containing nucleic acids.

Two variants of this method are used. Particularly short-chain nucleic acids are purified by bringing the starting material into contact with a chaotropic compound, with isopropanol and with a carrier material capable of binding nucleic acids. This alcohol is supposed to be present in a concentration of ≥5% (v/v) and lower than or equal to ≤40% (v/v). Thereby short-chain nucleic acids are supposed to bind more efficiently on the carrier material. The bound nucleic acids may remain on the carrier material, but may also be eluted. According to data in the published specification, short-chain nucleic acids are supposed to be purified particularly efficiently under these binding conditions (combination of chaotropic compound with isopropanol) and even enrichment of short-chain nucleic acids compared with longer-chain nucleic acids is supposed to be possible. However, the method does not describe any effective separation of short-chain and longer-chain nucleic acids. All fractions are purified. To achieve separation of short-chain and long-chain nucleic acids, a second method is described in this step. In this method the starting material is brought into contact with a chaotropic compound, with a branched and/or unbranched alcohol and with a carrier material capable of binding nucleic acids, wherein the alcohol is present in a concentration of ≤30% (v/v). Thereafter the breakthrough or supernatant from the first step is brought into contact with a chaotropic compound, with a branched and/or unbranched alcohol and with a carrier material capable of binding nucleic acids, wherein the alcohol is present in a concentration of ≥5% (v/v). It is stated that, under the conditions of the combination of a carrier material capable of binding nucleic acids with a chaotropic compound and an alcohol with a concentration of approximately 25%, this causes long-chain and longer-chain nucleic acids to bind preferentially, whereas the short-chain nucleic acids bind only very poorly and accordingly are found in the breakthrough/supernatant, from which they can then be isolated according to the described method. Even this second part of the method describes only the separation of longer-chain nucleic acids. There is no indication that fractionated isolation of short-chain and longer-chain/long-chain nucleic acids can be achieved. Also, the method does not permit any isolation of total nucleic acid and subsequent separation of short-chain and longer-chain/long-chain nucleic acids. What is decisive for the enrichment of short-chain nucleic acids is the combination of a chaotropic compound with preferably isopropanol.

Patent specification DE 102006045391 B4 likewise described a method that is suitable for the separation of long-chain and short-chain nucleic acids from a mixture containing these nucleic acids. In this case, separation takes place not by changing the binding conditions but instead via successive passes of the sample brought into contact with a chaotropic compound over two silicon dioxide phases having two different pore sizes. After two passes of the sample through silicon dioxide phase 1 and two passes of the sample through silicon dioxide phase 2, the nucleic acid fragments are separated in such a way that nucleic acid fragments with a size of at least 20,000 base pairs bind on the first phase and nucleic acid fragments with a size of at most 10,000 base pair bind on the second phase. This method is therefore not suitable for separation of short-chain and long-chain nucleic acids, which is precisely the stated objective of the present invention.

Published specification WO 2004/042058 A2 also belongs to the prior art. Therein it is disclosed that the pH of the binding buffers used has both a substantial influence on the yield of nucleic acids to be obtained and selectivity toward the fragment lengths of, for example, PCR products to be purified. In this case, it is not necessary to combine monovalent and multivalent salts with one another in one solution. Preferably, divalent salts and particularly preferably Mg or Ca salts are used. In the presence of binding buffers without alcohol, albeit with divalent cations, DNA fragments are recovered in quantitative amounts and over the size spectrum from 100 bp to 10,000 bp, preferably at a pH of >8.5.

The object underlying the present invention was to eliminate the disadvantages of the solutions described in the prior art.

The object has been achieved according to the features of the claims.

According to the invention, a method has been provided that makes it possible to purify and to isolate different size fractions of DNA selectively from a sample that contains a mixture of short-chain and longer-chain/long-chain nucleic acids (especially DNA), so that these fractions are available for further applications.

Moreover, a method has been provided that makes it possible to separate short-chain nucleic acids selectively from long-chain nucleic acids out of a sample that contains a mixture of short-chain and longer-chain/long-chain nucleic acids (DNA), wherein the size spectrum of the respective fraction is adjustable (e.g. separation of DNA smaller than 500 base pairs from DNA larger than 500 base pairs). The respective fraction that is not desired may then be discarded, while the desired fraction is subjected to further processing.

Furthermore, a method has been provided that makes it possible to concentrate short-chain and longer-chain/long-chain nucleic acids from a large-volume sample (e.g. plasma, serum, urine or other cell-free body fluids) and then to perform selective size-fractionated separation of nucleic acids as described under Point 1 or Point 2.

The present invention was based on an observation that the isolation of short-chain DNA fragments (DNA fragments smaller than 500 bp) from a PCR reaction mixture is always problematic when the amplification buffer used has a high pH and when a solution of a chaotropic buffer is used for purification.

The reason appears to be that a higher pH has a significant negative influence on the binding, especially of short-chain nucleic acids, on mineral carrier materials. If this were the reason, then the possibility would exist, via changing the pH, of being able to adjust binding conditions that would permit selective binding of short-chain or longer-chain/long-chain nucleic acids.

In contrast to the method described in published specification WO 2004/042058 A2, neither divalent or multivalent cations nor a combination of monovalent and divalent cations are necessary for isolation of nucleic acids of different lengths.

This is precisely what can be achieved very efficiently with the inventive method. Furthermore, the binding conditions can be adjusted so flexibly that any desired size fractionation of nucleic acids can be undertaken effectively. The inventive method therefore makes it possible to purify and to isolate different size fractions of DNA selectively from a sample that contains a mixture of short-chain and longer-chain/long-chain nucleic acids (DNA), or even to remove particular size fractions selectively. The workflow of the method is based on bringing a mixture of short-chain and longer-chain/long-chain nucleic acids into contact with a solution that contains a chaotropic salt. In order to achieve selective binding of short-chain or longer-chain/long-chain nucleic acids, the pH of this mixture is adjusted variably. It has been found that both short-chain and longer-chain/long-chain nucleic acids bind very efficiently on a mineral carrier material (e.g. glass-fiber filter material) at a pH of 6 or 7. After the nucleic acids have been bound on a mineral material (e.g. centrifugation column containing glass-fiber material), the carrier material is washed with washing buffers and finally, after addition of water or another buffer of low salt concentration, the bound nucleic acid fraction is eluted from the carrier. Surprisingly, it has been found that elevation of the pH of the mixture of the sample and of the aqueous solution of a chaotropic salt changes the size spectrum of the nucleic acids that bind on the carrier. Upon successive elevation of the pH, firstly short-chain nucleic acids no longer bind and then even longer-chain/long-chain nucleic acids do not bind and only long-chain nucleic acids remain on the carrier. This fractionation can be flexibly adjusted. Ultimately, longer-chain/long-chain or even only long-chain nucleic acids bind to the carrier material and short chain or short-chain/longer-chain nucleic acids do not. The bound nucleic acids may then be purified and isolated. Of much greater interest, however, are precisely the applications having the purpose of depleting longer-chain/long-chain nucleic acids from a mixture containing short-chain as well as longer-chain/long-chain nucleic acids and isolating the short-chain nucleic acids. Precisely this stated objective can be achieved simply and efficiently with the inventive method. After adjustment of the pH in the mixture of sample and chaotropic solution, longer-chain/long-chain nucleic acids bind on a first carrier material. The non-bound fraction of nucleic acids is then found in the respective filtrate.

Isolation of the short-chain nucleic acids contained in the filtrate takes place by means of the inventive method as follows. An aqueous solution having a pH lower than the pH that exists in the solution used for the first binding reaction is now mixed with the filtrate. As an example, this may be achieved solely by addition of a buffer solution (e.g. Tris HCl; pH 6) or else even by addition of nonionic surfactant, e.g. from the class of alkyl glycosides or octylphenol ethoxylates, or with a mixture of a chaotropic compound and a nonionic surfactant, etc. What is important for this purpose is merely that the resulting binding conditions be changed to such an extent that the nucleic acid fraction contained in the filtrate binds efficiently on a second carrier material. According to the invention, this is achieved by lowering the pH.

After the pH has been changed, the mixture is brought into contact with a second carrier capable of binding nucleic acids (e.g. a centrifugation column containing glass-fiber material), then is washed, and finally the nucleic acid is eluted from the carrier by addition of water or a buffer of low salt concentration.

It has been found that, by changing (lowering) the pH, the binding conditions are changed to the point that now the short-chain nucleic acids or if applicable the short-chain/longer-chain nucleic acids contained in the filtrate—the nucleic acid fraction that was not bound on the first carrier material—bind efficiently on the carrier material. Thus the present invention is based on a variable interaction of the flexible change of the binding conditions that exist for adsorption of nucleic acids on a first carrier material and the binding conditions that exist for adsorption of nucleic acids on the second carrier material. The binding conditions for the first carrier material are defined in such a way by a flexibly adjustable pH that any desired short-chain or longer-chain or long-chain nucleic acids bind on the first carrier material. After the extraction step has been completed, the non-bound fractions of the nucleic acids then remain in the filtrate. The binding conditions are now adjusted in such a way by addition of solutions of lower pH that these nucleic acids now bind on the second carrier material.

Surprisingly, it has also been found that the size fractionation does not represent percentage enrichment/depletion of particular fragment sizes by 20%, 50% or 60%, as described in the cited published specification EP2128169A1, but instead that this separation can even be achieved almost quantitatively (up to 99%/).

By means of the inventive method, therefore, two nucleic acid fractions can be separately isolated selectively and flexibly and are able to exist in parallel. If it is wished to have only one fraction and not both fractions, then the respective carrier material can be discarded, making it possible to process only the carrier material on which the desired nucleic acid fraction is present. Thus the desired enrichment/depletion of a selected nucleic acid size fraction can be adjusted and accomplished simply and efficiently.

However, the present invention of selective size fractionation of nucleic acid mixtures also makes it possible to process a biological sample containing different nucleic acid fractions directly. In particular, cell-free body fluids (serum, plasma, urine, etc.) are important starting samples, since so-called circulating cell-free DNA can be efficiently isolated from them. As already pointed out, what is important here is, for example, to deplete long-chain nucleic acids from the sample and to purify short-chain nucleic acids efficiently (e.g. to achieve separation of maternal and fetal DNA for a prenatal diagnosis). The inventive method also permits direct processing of such samples. For this purpose, a lysis/binding buffer consisting of the inventive combination of a chaotropic solution with a specifically and flexibly adjusted pH is mixed with the sample. In this case also, the changes of pH (the higher the pH at constant salt concentration, the less efficiently short-chain or subsequently longer-chain and long-chain nucleic acids are bound) can be adjusted so flexibly that a desired size fractionation can be defined. After brief lysis of the starting sample, the sample is brought into contact with a carrier capable of binding nucleic acids (e.g. centrifugation column containing glass-fiber material). In the process, the longer-chain/long-chain nucleic acids bind on this carrier and the shorter-chain species remain in the filtrate. The centrifugation column may now be discarded or be washed according to the already described workflow of the method, whereupon the bound longer-chain/long-chain nucleic acids are eluted from the carrier and are then available for further applications. The filtrate is then treated with a further solution in such a way that the resulting pH is now lower than the pH of the filtrate was before addition of this solution. As already explained, this may be achieved by addition of a Tris buffer or by addition of a salt solution or of a detergent or of an alcohol or even of mixtures of these components. This solution then permits binding of the nucleic acids contained in the filtrate on the second carrier material.

After washing steps, the short-chain nucleic acids are eluted and can be analyzed. By means of the inventive method, it is therefore possible to deplete the longer-chain/long-chain nucleic acids from the sample efficiently and to isolate the short-chain nucleic acids efficiently. The inventive method proves to be particularly useful by the fact that it is also possible to process large-volume biological samples in such a way that size fractionation of nucleic acids is possible. In this connection, the testing of cell-free body fluids is in turn of increasing interest. As already described, circulating nucleic acids are very interesting for a large number of diagnostic issues. However, the concentration of this cell-free circulating DNA is very low, and so the possibility of processing of large sample volumes is very desirable, since in this way a significant enhancement of the yields of DNA can be achieved. Patent disclosure (WO2009/055596) describes an efficient and very simple method for enrichment of cell-free DNA from large-volume samples. A commercially available kit (PME free-circulating DNA Extraction Kit; Analytik Jena AG) may even be used for this enrichment and subsequent purification of cell-free DNA. However, this method permits only purification of the cell-free circulating total DNA. It does not permit any separation of short-chain and long-chain nucleic acids. In this case, the present invention offers a solution. For example, it is possible to combine the enrichment step for cell-free DNA with subsequent size-fractionation of short-chain and longer-chain/long chain nucleic acids. Thus the possibility of processing large sample volumes and also of permitting size fractionation exists for the first time. For the subsequent performance of this inventive method, the cell-free total DNA of a sample is enriched in a first step. For this purpose, an aqueous alginate solution and an aqueous solution containing salts of divalent or polyvalent cations (e.g. calcium chloride or aluminum chloride) are added to the sample. After brief centrifugation, the large-volume supernatant is removed and further processing takes place with the resulting pellet. This pellet contains the cell-free total DNA.

The pellet is now dissolved with a buffer and then the conditions are adjusted to permit efficient adsorption of the enriched cell-free total DNA on a first carrier material (e.g. centrifugation column containing glass-fiber material). After washing steps, the cell-free total DNA is eluted from this first carrier material. In this way, the resulting eluate contains short-chain and longer-chain/long-chain nucleic acids. A small volume is removed from this eluate. The remaining volume is now further processed according to the already described inventive method. A chaotropic solution, the pH of which has been adjusted according to the invention in such a way that a desired nucleic acid fraction (longer-chain/long-chain nucleic acid) binds on the second carrier material (the adjustment of the pH determines which fragment lengths of the total DNA will bind on the carrier material or which fraction will not bind and will therefore be contained in the filtrate) is added to the eluate. This mixture is then brought into contact with a carrier capable of binding nucleic acids (e.g. a centrifugation column containing a glass-fiber material). Thereupon the carrier material is washed with washing buffers and finally, after addition of water or another buffer of low salt concentration, the bound nucleic acid fraction is eluted from the carrier. According to the invention, this second eluate now contains the fraction of the longer-chain/long-chain nucleic acid. The short-chain nucleic acids present in the filtrate are then again isolated by addition of a solution having a lower pH than the pH used for the previous binding to the carrier material. It is now ensured according to the invention that the nucleic acids present in the filtrate can bind on a third carrier material and be isolated. Thereupon the mixture is brought into contact with a third carrier capable of binding nucleic acids (e.g. a centrifugation column containing glass-fiber material), then is washed, and finally the nucleic acid is eluted from the carrier by addition of water or a buffer of low salt concentration. In this way the third fraction—the short-chain nucleic acids—is then obtained in this eluate. The inventive method makes it possible for the first time to obtain three different nucleic acid fractions simultaneously and in parallel from one sample. These different fractions can now be investigated.

The invention will be explained hereinafter on the basis of exemplary embodiments.

However, these exemplary embodiments do not represent any limitation of the invention.

EXEMPLARY EMBODIMENT 1

Selective size-fractionated isolation of DNA from a sample that contains a mixture of different DNA fragments. Explanation of how the change of pH of the mixture of sample and chaotropic salt solution influences the DNA size selectivity.

Respectively 40 µL of a sample containing a DNA ladder (DNA fragments with a broad size spectrum) was mixed with 400 µL of a chaotropic compound (4 M guanidine isothiocyanate). The pH was adjusted/changed by addition of a Tris HCl solution with different pH values (pH 6.0, pH 7.0, pH 7.5, pH 8.0, pH 9.0). The concentration of the Tris solution in the binding mixture was respectively 10 mM. Only the chaotropic salt solution was mixed with the sample.

All reaction mixtures were centrifuged using a centrifugation column (containing glass-fiber material). The centrifugation columns were then washed with an alcoholic washing buffer and dried by a centrifugation step, and the bound nucleic acid was eluted by addition of water.

The isolated DNA fragments were detected by means of an Agilent Bioanalyzer, using DNA kit 7500 (FIGS. 1-6). This permits sensitive and quantitative detection of the isolated DNA fragments. In this connection, it is obvious that, upon addition of Tris HCl with a pH of 6.0 and 7.0, all DNA fragments contained in the sample bind efficiently, and do so even somewhat more strongly than is the case with the pure chaotropic salt solution. If Tris solutions with a pH of 7.5, 8.0 and 9.0 are then mixed with the sample and thus the pH of the binding mixture is further raised, then it is obvious that these binding conditions are no longer sufficient to bind the smaller fragments or that the binding is completely inhibited. After addition of a Tris solution with a pH of 7.5, only fragments larger than 200 bp are bound efficiently. After addition of a Tris solution with a pH of 8.0, only fragments of approximately 1000 bp are bound efficiently. After addition of a Tris solution with a pH of 9.0, none of these fragments binds any longer.

EXPLANATION OF THE FIGURES

Figure 4:
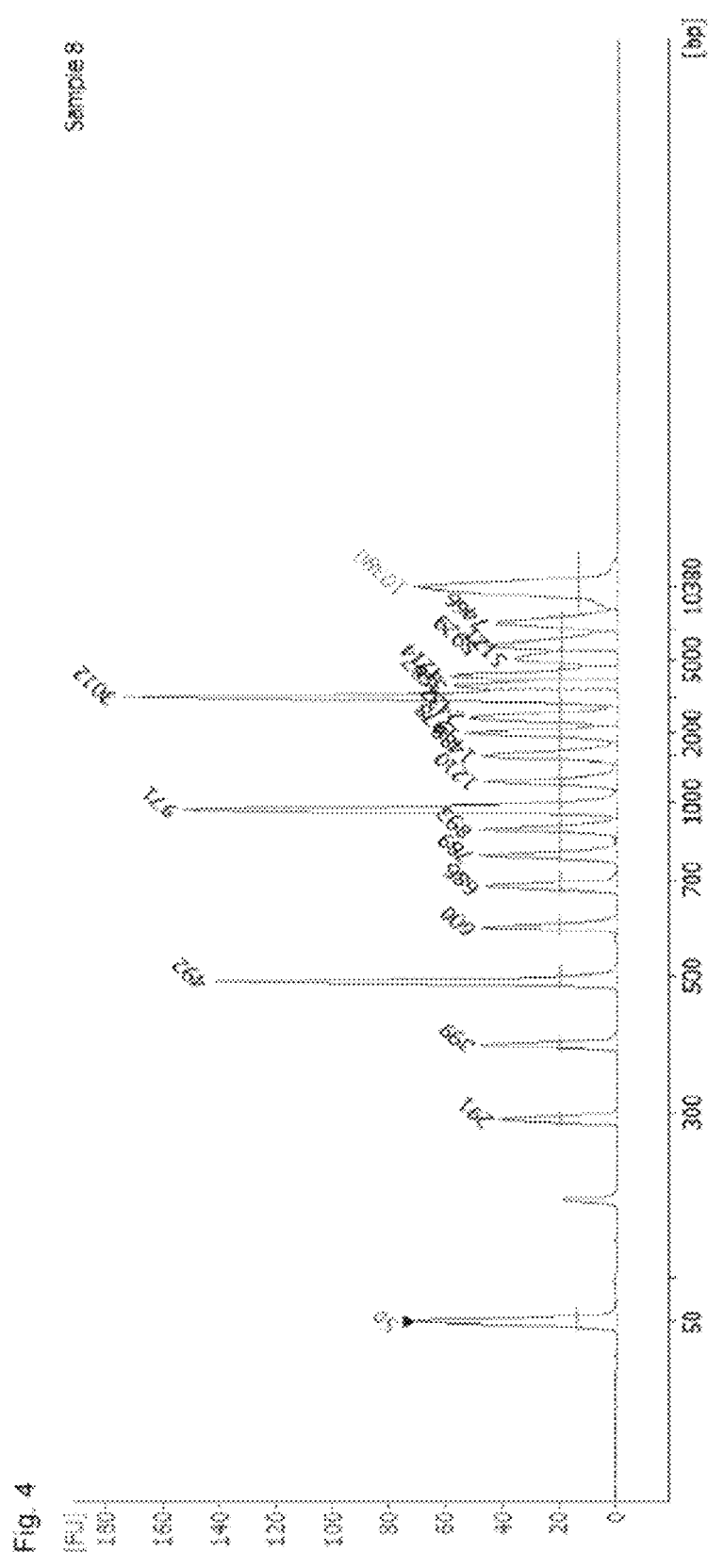

FIG. 4 shows an Agilent Bioanalyzer analysis (sample+chaotropic salt solution+Tris solution with pH 7.5).

EXEMPLARY EMBODIMENT 2

Selective size-fractionated isolation of DNA from a sample that contains a mixture of different DNA fragments, with the objective of isolating fragments>300 bp in the first fraction and fragments<300 bp in the second fraction.

Respectively 40 µL of a sample containing an aqueous solution with a DNA fragment of approx. 100 bp, a DNA fragment of approx. 300 bp and a DNA fragment of approx. 1000 bp was mixed with 400 µL of a chaotropic compound (4 M guanidine isothiocyanate; 5 mM Tris HCl, pH 7.5). In conformity with the stated objective of the experiment, 9 µL 0.05 N NaOH was added to the mixture of sample and chaotropic solution in order to adjust the pH such that the desired fractionation was achieved.

All reaction mixtures were centrifuged using a first centrifugation column (containing glass-fiber material). The centrifugation columns were then washed with an alcoholic washing buffer and dried by a centrifugation step, and the bound nucleic acid was eluted by addition of water.

200 µL of a 2 M Tris-HCl solution (pH 6.0) was mixed with the filtrate, and this mixture was transferred to a second centrifugation column (containing glass-fiber material) and centrifuged. The centrifugation column was then washed with an alcoholic washing buffer and dried by a centrifugation step, and the bound nucleic acid was eluted by addition of water.

The fractionated DNA fragments were detected by means of an Agilent Bioanalyzer, using DNA kit 7500. This permits sensitive and quantitative detection of the isolated DNA fragments.

Figure 1:
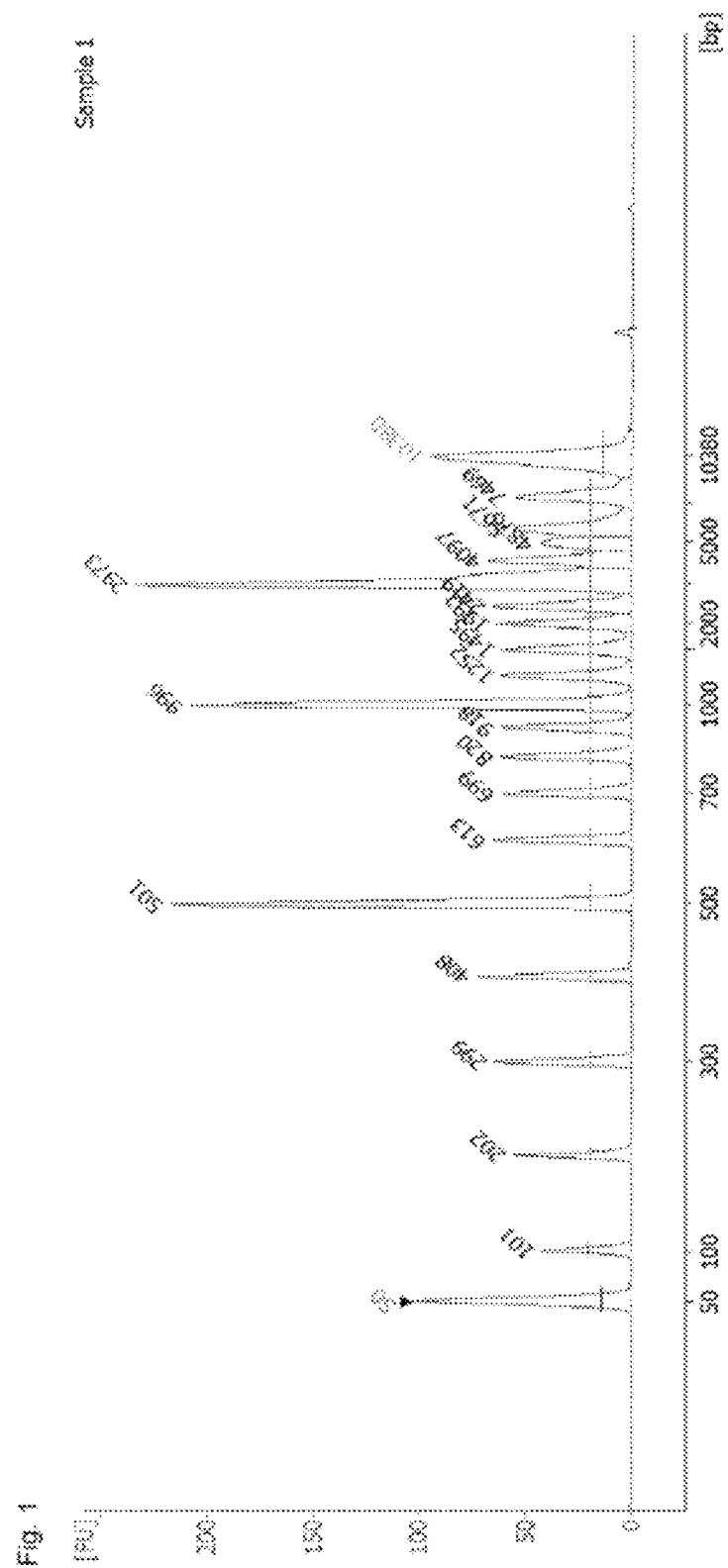
FIG. 1 shows an Agilent Bioanalyzer analysis (sample+chaotropic salt solution).
Figure 2:
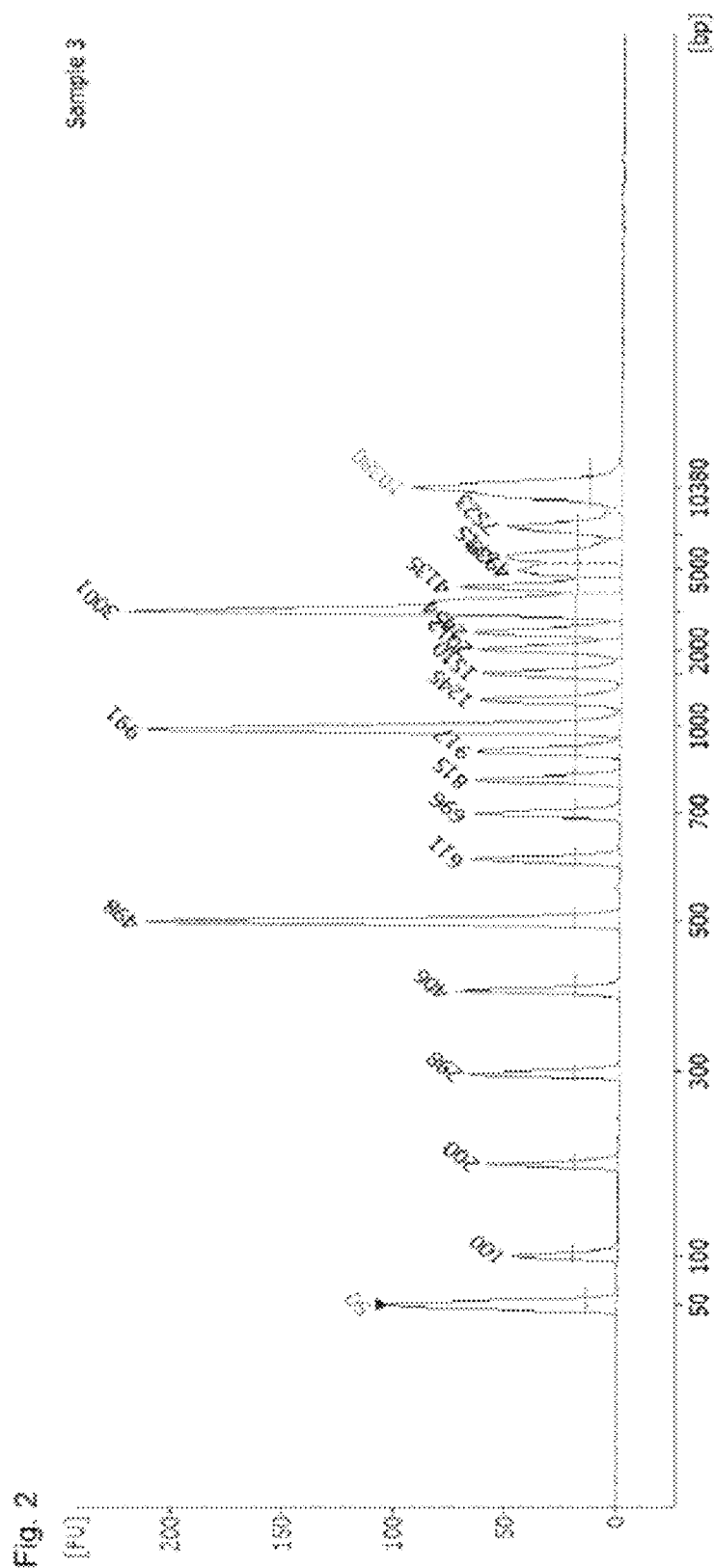
FIG. 2 shows an Agilent Bioanalyzer analysis (sample+chaotropic salt solution+Tris solution with pH 6.0).
Figure 3:
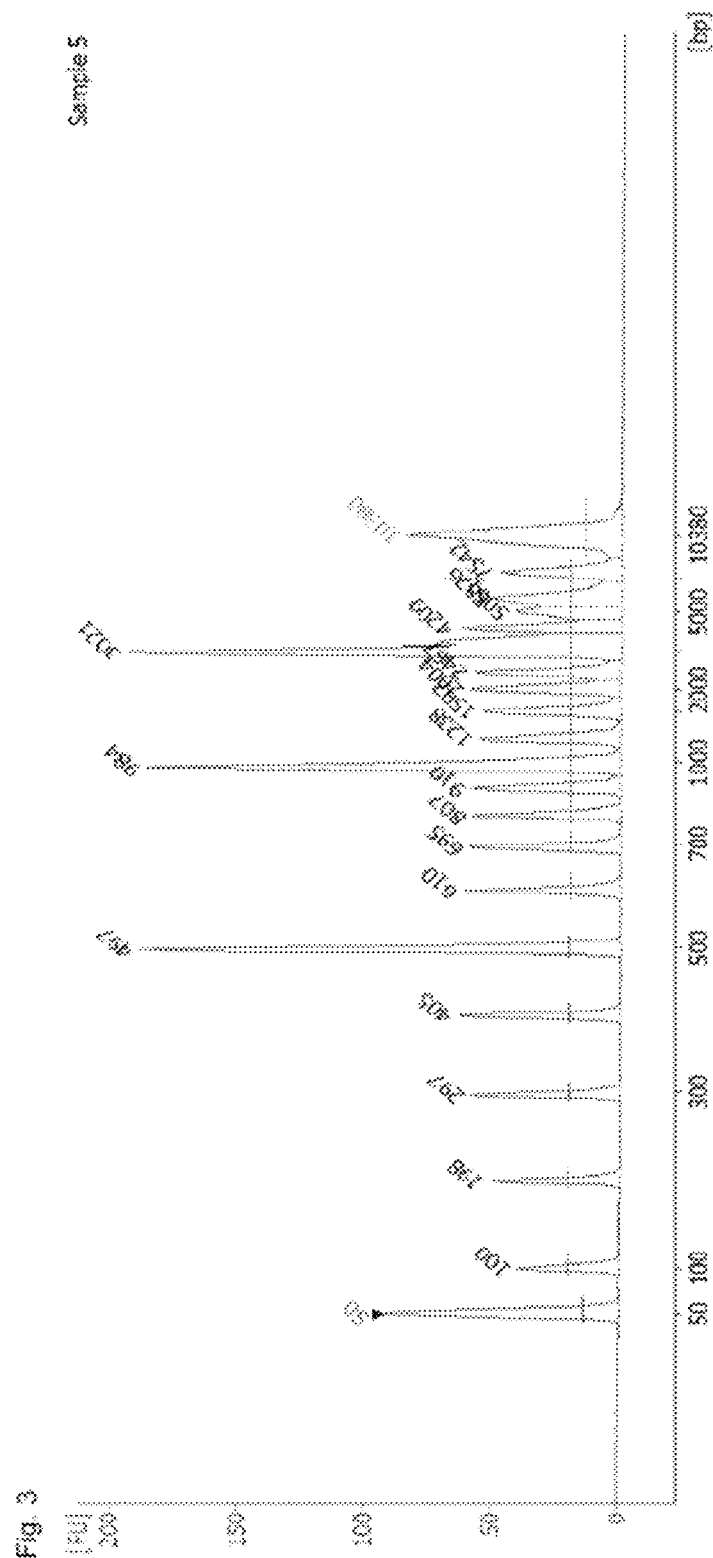
FIG. 3 shows an Agilent Bioanalyzer analysis (sample+chaotropic salt solution+Tris solution with pH 7.0).
Figure 5:
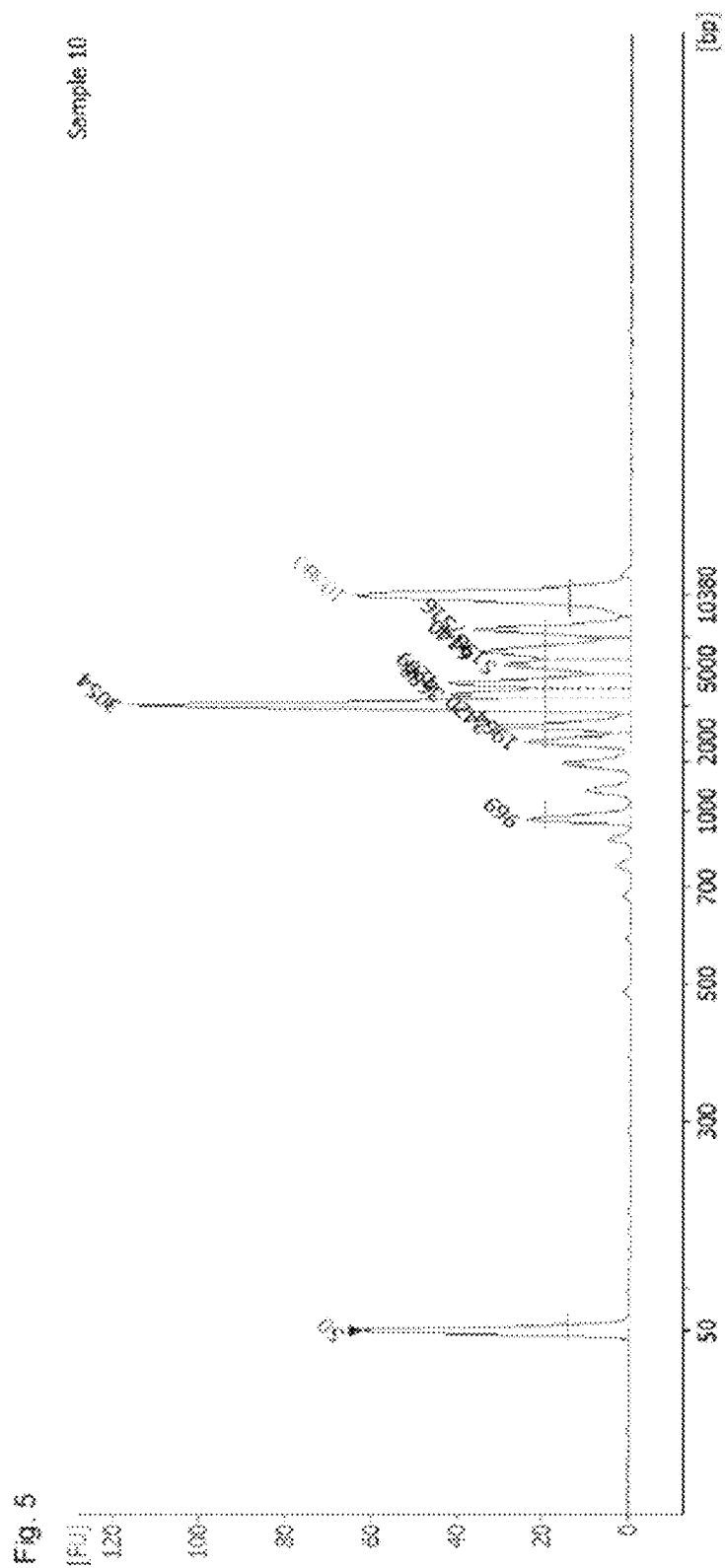
FIG. 5 shows an Agilent Bioanalyzer analysis (sample+chaotropic salt solution+Tris solution with pH 8.0).
Figure 6:
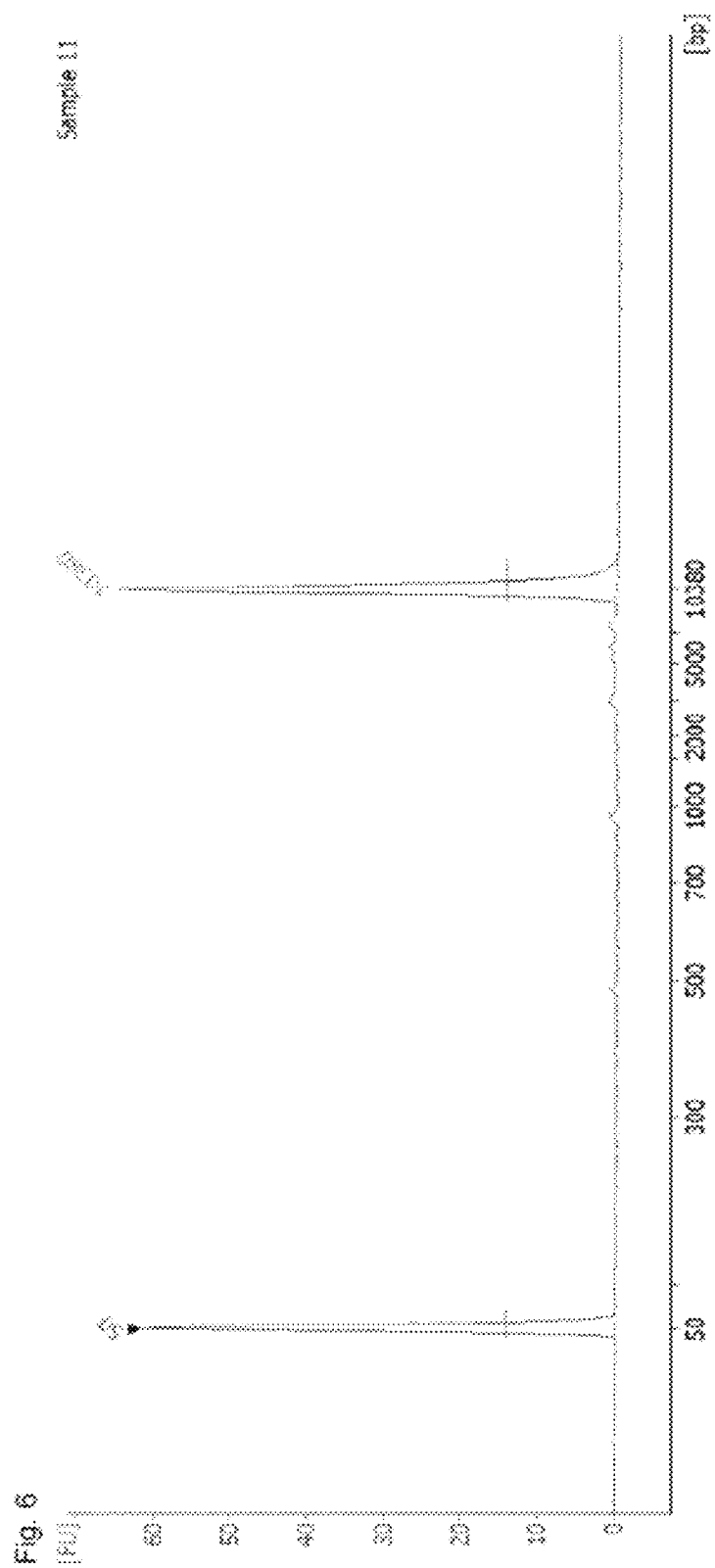
FIG. 6 shows an Agilent Bioanalyzer analysis (sample+chaotropic salt solution+Tris solution with pH 9.0).
Figure 7:
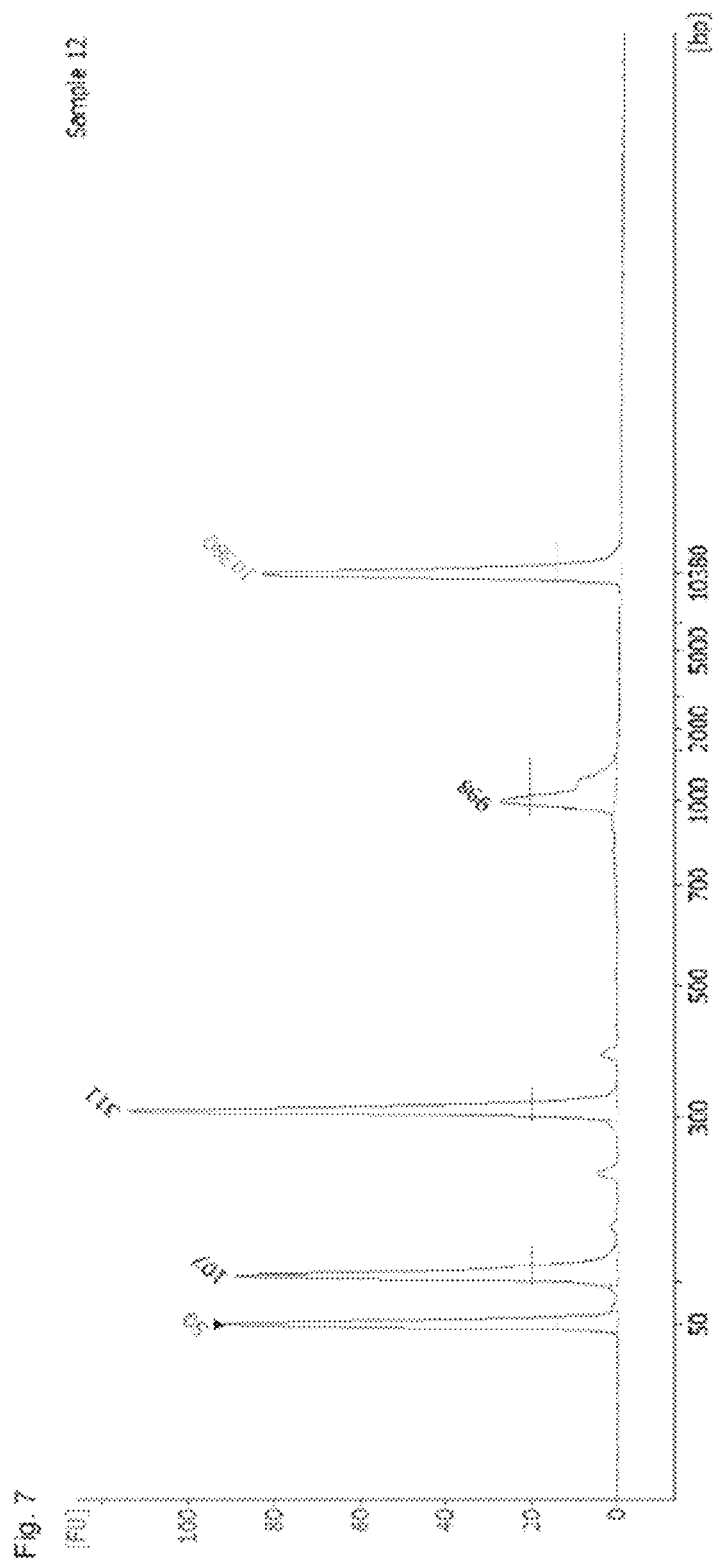
Figure 8:
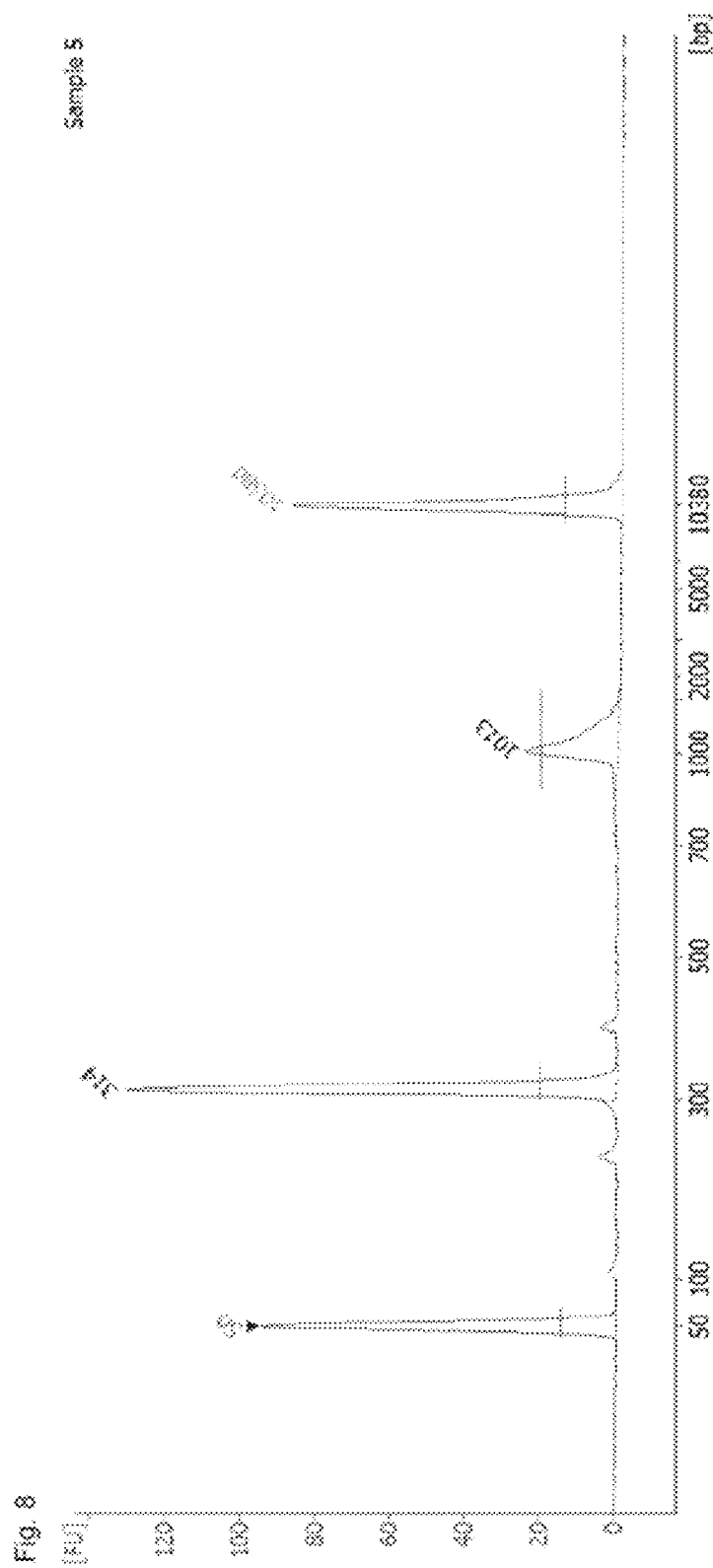
Figure 9:
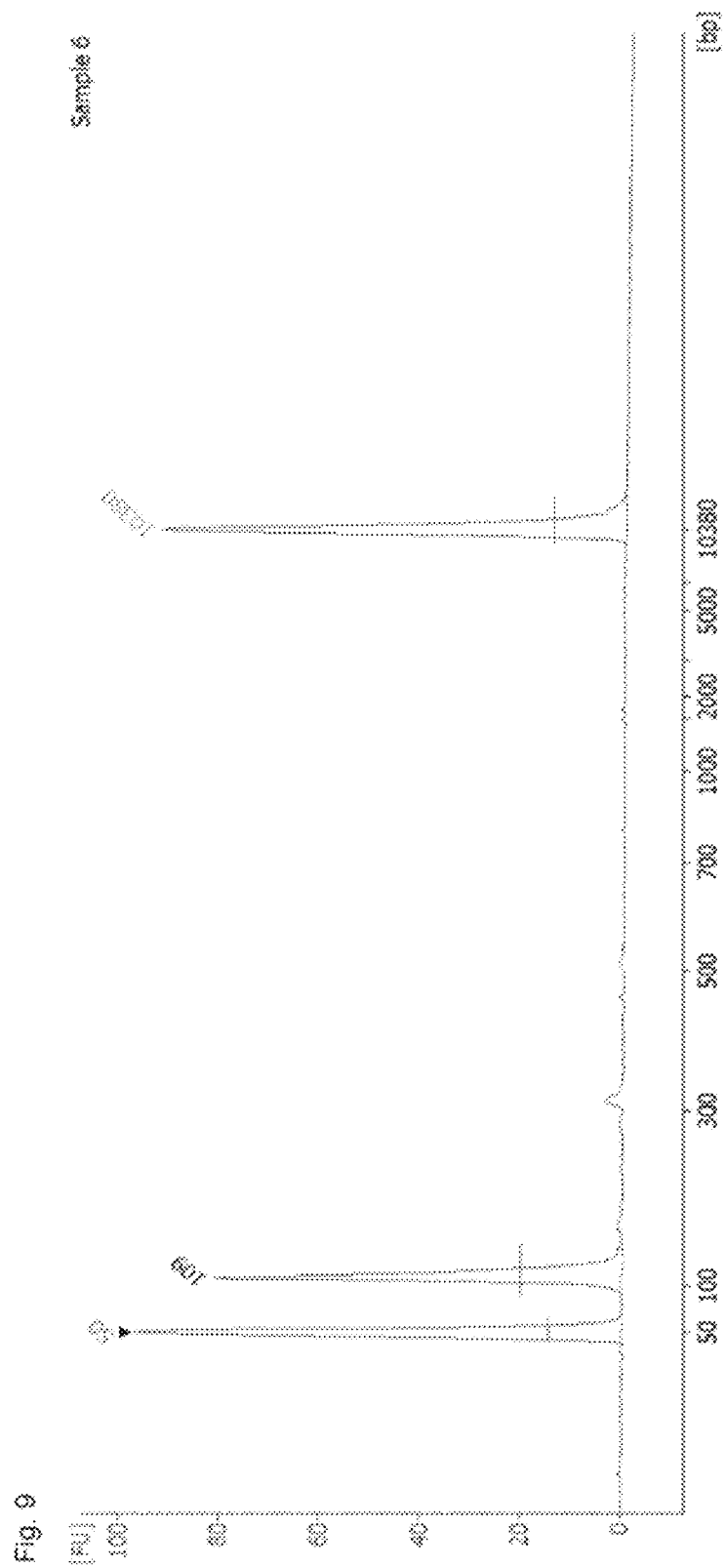

The following FIGS. 7-9 clearly show how efficient the separation of the nucleic acid fragments from the initial mixture is. The first fraction (eluates of the first centrifugation column) contains the 300-bp and 1000-bp fragments but not the 100-bp fragment. The second fraction (eluate of the second centrifugation column) contains the 100-bp fragments but not the 300-bp and 1000-bp fragments. This experiment shows impressively how selectively the inventive method functions, since separation of fragments larger than 300 bp from fragments smaller than 300 bp takes place efficiently.

FIG. 7 shows an Agilent Bioanalyzer analysis (sample containing the three different DNA fragments).

FIG. 8 shows an Agilent Bioanalyzer analysis (eluate of the first fraction containing the longer-chain DNA fragments).

FIG. 9 shows an Agilent Bioanalyzer analysis (eluate of the second fraction containing the short-chain DNA fragment).

EXEMPLARY EMBODIMENT 3

Selective Size-Fractionated Isolation of DNA Directly from a Plasma Sample.

The objective of the example was to show that size-fractionated isolation of DNA directly from a biological sample is also possible, i.e. that it is possible to separate short-chain nucleic acids from longer-chain/long-chain nucleic acids efficiently and to process both fractions in parallel, or, if only one fraction is desired, to remove the other fraction from the sample efficiently, so that it has no interfering influence on specific applications.

Starting samples were respectively 200 µL of a plasma sample containing short-chain nucleic acid fragments (51 bp, 77 bp, 103 bp, 149, bp, 199, bp, 298, bp) and a longer-chain fragment of 1118 bp. The intention was to show that the short-chain fraction can be separated from the longer-chain fraction.

300 µL of a chaotropic compound (4 M guanidine isothiocyanate, 5 mM Tris HCl, pH 7.5) was mixed with the samples. Furthermore, a nonionic surfactant from the class of alkyl glucosides and 20 µL Proteinase K (20 mg/mL) were added to the sample. The sample was lysed for 15 minutes at 70° C. For adjustment of the pH necessary for the intended selective separation of the nucleic acid fragments, 4 µL of a Tris-HCl solution with pH 8 was added to the solution. Then the mixture was centrifuged using a first centrifugation column (containing glass-fiber material). 400 µL of a mixture of a chaotropic compound and a nonionic surfactant from the class of alkyl glucosides (4 M guanidine isothiocyanate/30% nonionic surfactant) was mixed with the filtrate, in order to establish the specific binding conditions for adsorption of the short-chain nucleic acid fragments contained in the filtrate. This mixture was transferred to a second centrifugation column (containing glass-fiber material) and centrifuged.

Both centrifugation columns were then washed with ethanolic washing buffers and finally the bound nucleic acid was eluted with water.

The isolated DNA fragments were again detected by means of an Agilent Bioanalyzer, using DNA kit 7500. The evaluation shows that size-fractionated separation of DNA directly from a biological sample is possible. In this example, the binding conditions for the first centrifugation column and for the second centrifugation column were adjusted such that fragments, the short-chain nucleic acid fragments, were not bound on the first column, and that these shorter-chain fragments are then in the filtrate and can be isolated via the second centrifugation column. Thus it has been possible to show that longer-chain nucleic acids can be removed efficiently from a sample or that, depending on stated objective, both fractions can be processed in parallel and be available. The Agilent Bioanalyzer analyses are plotted on the following FIGS. 10 and 11.

Figure 10:
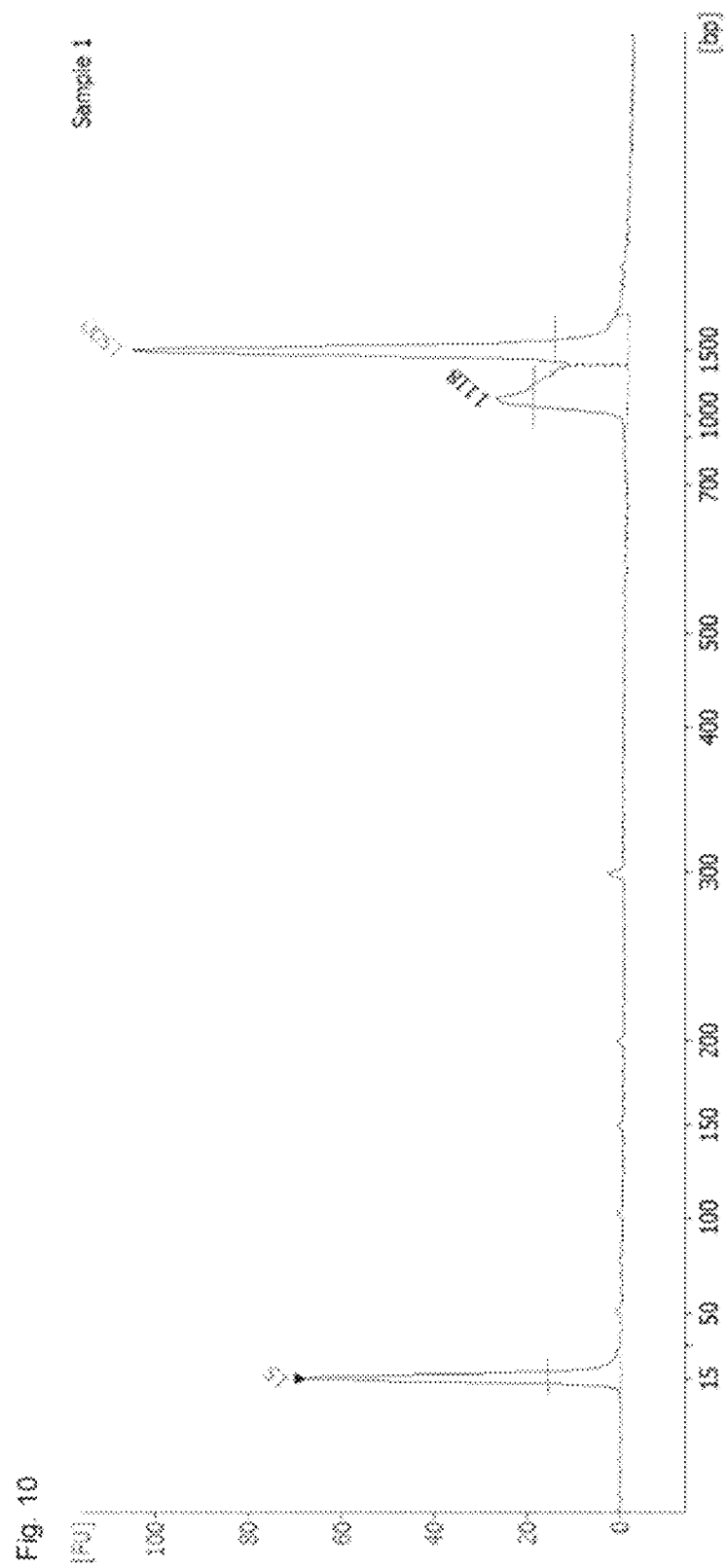

FIG. 10 shows an Agilent Bioanalyzer analysis (eluate of the first fraction containing the longer-chain DNA fragment).

Figure 11:
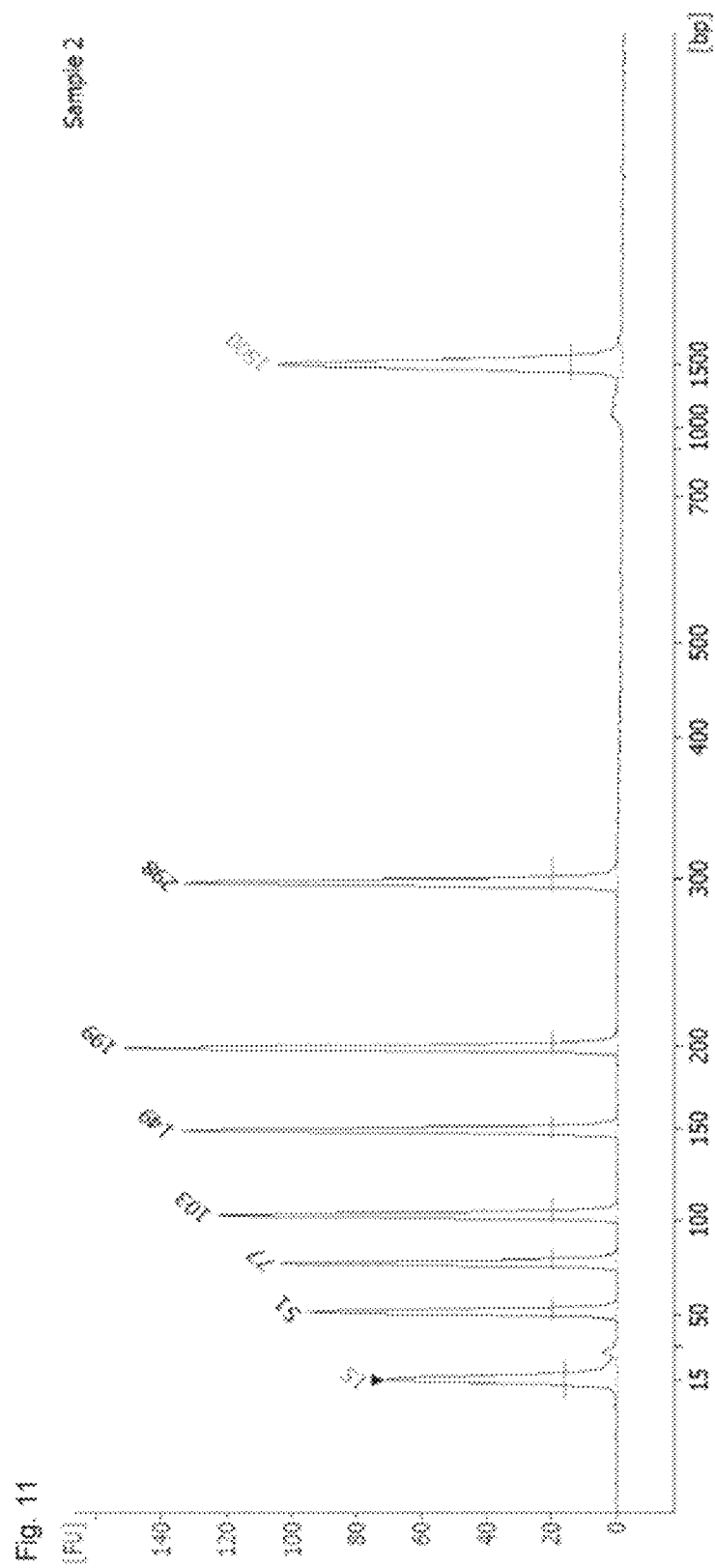

FIG. 11 shows an Agilent Bioanalyzer analysis (eluate of the second fraction containing the short-chain DNA fragments).

EXEMPLARY EMBODIMENT 4

Enrichment of cell-free DNA from a human plasma sample and subsequent selective separation of the short-chain and longer-chain/long-chain nucleic acids, differential isolation of the two fractions and measurement of the depletion of the short-chain nucleic acids from the longer-chain/long-chain nucleic acids by means of real-time PCR. Explanation of the influence of successive elevation of the pH for selective binding on the first filter column and the corresponding filtrate.

The starting material was a 1-mL human plasma sample. The enrichment of the DNA fragments was carried out using a commercially available kit (PME free-circulating DNA Extraction Kit; Analytik Jena AG) and following the manufacturer's instructions. After the enrichment step, the cell-free total nucleic acid was isolated according to the manufacturer's instructions.

The eluate containing the isolated total nucleic acid was then used for selective separation of the short-chain from the longer-chain/long-chain nucleic acid fraction. 4 separate mixtures were tested. The binding conditions were selected such that even the longer-chain nucleic acids would be bound increasingly less efficiently on the first centrifugation column as the pH was successively raised, so that thereby even longer-chain nucleic acid would then remain in the filtrate and ultimately would then bind subsequently on the second column.

The eluate (40 µL) obtained after enrichment and extraction and containing the total nucleic acid of cell-free DNA was mixed with 400 µL of a chaotropic compound (4 M guanidine isothiocyanate; 5 mM Tris HCl, pH 7.5). The pH was influenced by addition of 1 µL 0.1 N NaOH (sample 1), 5 µL 0.1 N NaOH (sample 2), 10 µL 0.1 N NaOH (sample 3), 20 µL 0.1 N NaOH (sample 4).

Then the mixture was centrifuged using a first centrifugation column (containing glass-fiber material). The centrifugation column was stored. For isolation of the short-chain DNA, 400 µL of a mixture of a chaotropic compound and a nonionic surfactant from the class of alkyl glucosides (4 M guanidine isothiocyanate/30% nonionic surfactant, 50 mM Tris HCl, 6.0) was mixed with the filtrate, and this mixture was transferred to a second centrifugation column (containing glass-fiber material) and centrifuged. The two centrifugation columns were then washed with an alcoholic washing buffer and dried by a centrifugation step, and the bound nucleic acid was eluted by addition of water. The eluted nucleic acid fractions were then tested in a real-time PCR.

For this purpose a SybrGreen-based real-time PCR was performed for amplification of a cytochrome b fragment with a size of approximately 1 kb. Both eluate fractions from the respective two samples were used for the PCR.

PCR Primer Used:

CyB S:
CCA GCY CCA TCA AAC ATC TCA KCA TGA TG

CyB AS:
TTG GCT GAG TGG TCG GAA TAT TAT GCT KCG TTG YTT

Reaction Mixture (Amplification/Hybridization)
Per Sample:

| | |
|---|---|
| sense primer (50 pmol/µL) | 0.1 µL |
| antisense primer (50 pmol/µL) | 0.1 µL |
| SyGreen MasterMix (AJ) | 7.5 µL |
| PCR-grade H₂O | add 15 µL |

The PCR was performed in a commercial real-time PCR cycler:
Amplification Conditions

| | | |
|---|---|---|
| Step 1: | Denaturing | 95° C. 120 minutes |
| Step 2: | Amplification | 45 cycles |
| | | 95° C. 4 minutes |
| | | 55° C. 40 minutes |

Then a melting-point analysis curve was plotted to demonstrate the application specificity. The PCR results are plotted graphically in FIG. 12. The smaller the Ct values, the higher is the proportion of the respective nucleic acid fraction in the sample. It can be clearly seen how efficiently longer-chain nucleic acids can be removed from the short-chain fraction.

Thus the proportion of longer-chain nucleic acids in sample 1 is hardly even 1%, i.e. the depletion is greater than approximately 99%. It can also be clearly seen how the proportions of the longer-chain nucleic acids are shifted into fraction 2 when the pH for binding on the first column is raised.

Figure 12:
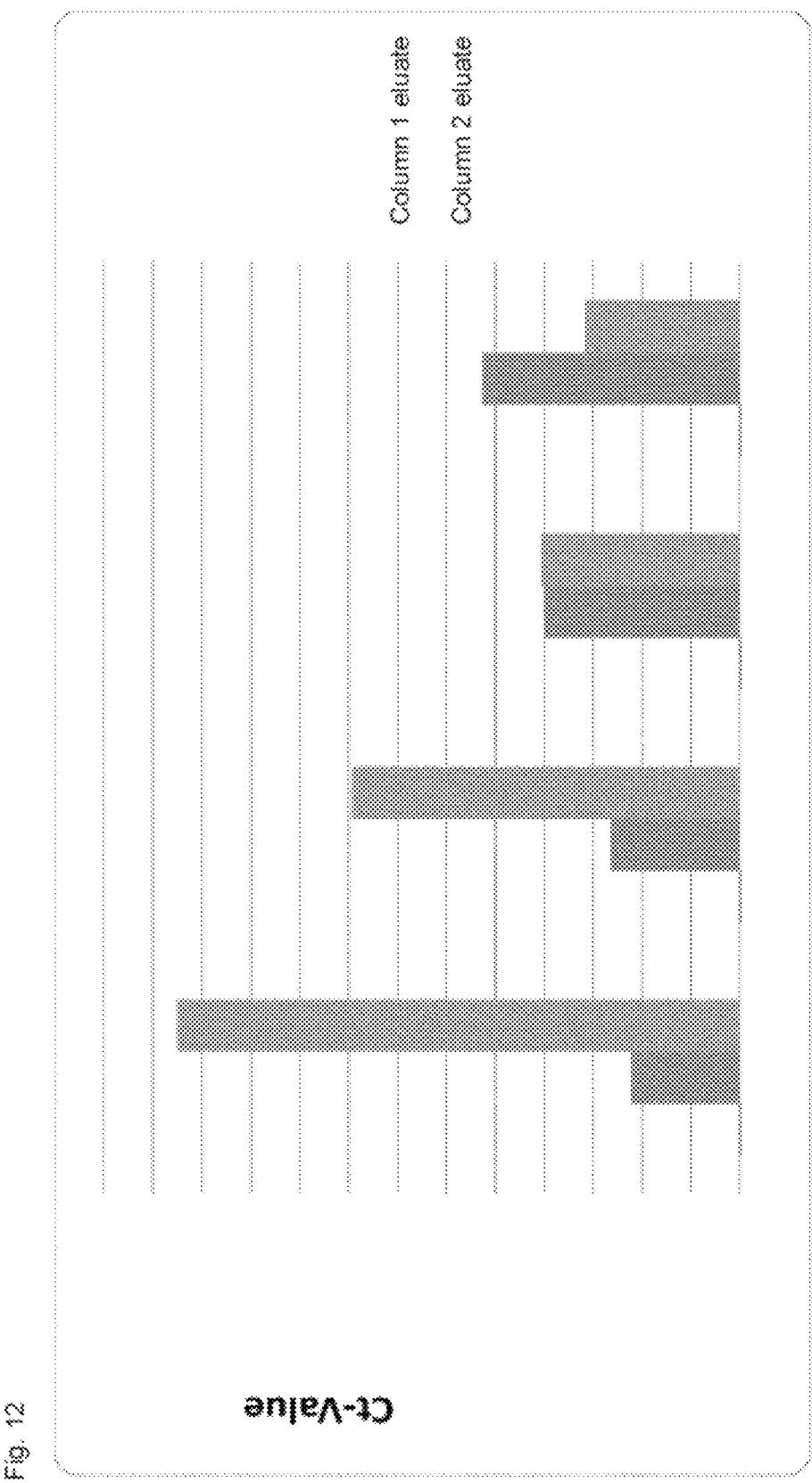

FIG. 12 shows the graph of the Ct values.

DEFINITIONS

Chaotropic Substances or Chaotronic Salts:
Substances that disrupt the regular structure—which is based on hydrogen bonds—of liquid water, by inhibiting formation of the H2O cage structure necessary for solvation. Examples of chaotropic constituents are thiocyanates, iodides or perchlorates. They bring about denaturing of proteins, an increase in solubility of nonpolar substances in water, and disruption of the hydrophobic interaction.

Aliphatic Alcohols
Aliphatic alcohols within the meaning of this patent description and claims are all alcohols that carry their OH group on an aliphatic C atom, with the exception of amino alcohols such as TRIS.

The invention claimed is:

1. A method for fractionated size-dependent isolation of a nucleic acid from a mixture of nucleic acids with different numbers of base pairs, the method comprising:
   a) adding, in the absence of an aliphatic alcohol, a first binding buffer, which comprises at least one chaotropic salt and at least one substance that raises the pH of the binding buffer to a volume of the mixture of nucleic acids;
   b) binding on a first solid phase and separation of the nucleic acids bound to said first solid phase, from a filtrate;
   c) mixing a second binding buffer, which has a lower pH than the first binding buffer, with the filtrate from said b) binding; wherein said second binding buffer comprises at least one selected from the group consisting of a nonionic surfactant and an alcohol;
   d) binding on a second solid phase and separation of the nucleic acids bound to said second solid phase;
   e) washing and elution of the nucleic acid isolated after said b) binding and said d) binding,
   with the result that the nucleic acid isolated after said b) binding not only has a larger number of base pairs than a nucleic acid isolated under said d) binding, but also that, both after both said b) binding and after said d) binding, individual, particular nucleic acid fractions with a particular number of base pairs are isolated that were not isolated in the respective other step wherein,
   prior to fractionation, first of all the total nucleic acid is concentrated in a sample volume of any desired size by reducing said sample volume.

2. The method according to claim 1, wherein the second binding buffer comprises at least one chaotropic substance.

3. The method according to claim 1, wherein said chaotropic salt comprises 4 M of guanidine isothiocyanate; and said substance that raises the pH of the binding buffer comprises NaOH.

4. The method according to claim 1, said alcohol comprises an aliphatic alcohol; and said nonionic surfactant comprises at least one member selected from the group consisting of an alkyl glucoside and an octylphenol ethoxylate.

5. The method according to claim 1, wherein the size of a nucleic acid (number of base pairs) isolated after said b) binding is controlled by the stepwise elevation of the pH of the binding buffer according to said a) adding, with the result that fewer short chain nucleic acids having less than 500 bp (smaller number of base pairs) can be separated as the pH is raised.

6. The method according to claim 1, wherein the size of a nucleic acid (number of base pairs) isolated from said b) binding is controlled by the stepwise lowering of the pH in the filtrate from said b) binding or by addition of a nonionic surfactant or of an alcohol or of a mixture of nonionic surfactant and alcohol to the first binding buffer, with the result that more short chain nucleic acids having less than 500 bp (smaller number of base pairs) can be separated with increasing concentration of the added substance.

7. The method according to claim 1, further comprising: isolating a fraction of nucleic acids having one of the following distribution of sizes:
   a) less than or equal to 110 base pairs;
   b) less than or equal to 150 base pairs;
   c) less than or equal to 550 base pairs; and
   d) greater than or equal to 1,000 base pairs.

8. The method according to claim 1, wherein the mixture of nucleic acids with different numbers of base pairs is a mixture comprising at least one short-chain nucleic acid having less than 500 bp and at least one long-chain nucleic acid having 500 bp or more.

* * * * *